United States Patent [19]
Jervis

[11] Patent Number: 5,816,258
[45] Date of Patent: Oct. 6, 1998

[54] BLADDER NECK SUSPENSION METHOD

[75] Inventor: James E. Jervis, Atherton, Calif.

[73] Assignee: General Surgical Innovations, Inc., Cupertino, Calif.

[21] Appl. No.: 664,051

[22] Filed: Jun. 13, 1996

[51] Int. Cl.$^6$ .................................................. A61B 19/00
[52] U.S. Cl. .................. 128/898; 606/139; 128/DIG. 25
[58] Field of Search ............................. 128/898, DIG. 25, 128/885; 606/139, 144, 148, 145, 151; 600/30, 29, 31, 37; 112/169; 289/1.2

[56] References Cited

U.S. PATENT DOCUMENTS

| | | | |
|---|---|---|---|
| 5,391,176 | 2/1995 | De La Torre ............................. | 606/148 |
| 5,496,335 | 3/1996 | Thomason et al. . | |
| 5,496,345 | 3/1996 | Kieturakis et al. ....................... | 606/192 |
| 5,527,323 | 6/1996 | Jervis et al. .............................. | 606/148 |
| 5,544,664 | 8/1996 | Benederev et al. ...................... | 128/898 |
| 5,562,685 | 10/1996 | Mollenauer et al. .................... | 606/144 |
| 5,582,188 | 12/1996 | Benderev et al. ........................ | 128/898 |

OTHER PUBLICATIONS

General Surgical Innovations, Inc., KnotMaker™ knot placement device, ©1994.
Fiorelli et al. "Simplified endoscopic suspension for stress incontinence through pervaginal route." Arch Esp de Urol 44(1):101–104, 1991.
Knapp, Jr. et al. "Laparoscopic retroperitoneal needle suspension urethropexy." J Endourol 8(4):279–284, 1994.
Jarvis, G.J. "Long needle bladder neck suspension for genuine stress incontinence." Brit J Urol 76: 467–469, 1995.
Tay et al. "Laparoscopic bladder neck suspension for urinary stress incontinence in women." Int J Urol 3: 278–281, 1996.
Iosif, C. S. "Laparoscopic surgery for stress urinary incontinence." Urol Int 57: 180–184, Oct. 1996.

*Primary Examiner*—Vincent Millin
*Assistant Examiner*—Kelly O'Hara
*Attorney, Agent, or Firm*—Lyon & Lyon LLP

[57] ABSTRACT

A laparoscopic bladder neck suture suspension procedure that anchors a suture in Cooper's ligament and, transvaginally, in the anterior vaginal wall to provide upper and lower suspension points and, then, ties and tensions a knot intracorporeally within the retropubic space between the upper and lower suspension points. The laparoscopic bladder neck suture suspension procedure utilizes a surgical instrument that combines a knot tying device mounted over a suture passing device. The suture passer may incorporate a grasper at its tip for purposes of passing a suture through body tissue as desired. The knot tying device is used to suture intracorporeally under tension using sliding knots such that the tension can be increased incrementally as the surgeon tests the elevation of the bladder neck by feel.

19 Claims, 9 Drawing Sheets

BLADDER NECK SUSPENSION METHOD

FIELD OF THE INVENTION

This invention relates to endoscopic surgery, and more particularly, to a procedure and instrumentation that facilitates laparoscopic bladder neck suture suspension.

BACKGROUND OF THE INVENTION

Millions of women thirty (30) years or older suffer from stress urinary incontinence ("SUI") on a daily basis. SUI causes the uncontrollable loss of urine due to a displacement of the bladder. Depending on the severity of incontinence, there are a number of treatment options for SUI, including collagen injections, drugs, biofeedback exercises and absorbent pads. For severe SUI, an open surgical procedure involving suture suspension of the bladderneck (urethropexy) has been the standard method of treatment for decades. This method, however, is invasive and can create significant complications for the patient, including enterocele (a hernia within the vaginal wall) and genital prolapse (a descending of the uterus due to a weakness of the pelvic floor). Furthermore, after surgery patients may require up to six weeks or more to resume their preoperative lifestyle. Because of the risk, expense and complexity of suture suspension, this open surgical procedure is often considered an undesirable option for the treatment of SUI.

Several minimally invasive surgical alternatives have been developed to suspend the bladderneck. However, these minimally invasive bladder neck suture suspension procedures present surgeons, especially new-comers to the field, with a daunting array of skill and judgement requirements. For instance, the bladder must be properly positioned in order to assure both urinary continence and voluntary voiding within a reasonable time. Proper bladder positioning requires experience and proctoring. Another area of difficulty is the means of accomplishing an upper suspension. There must be a reliable upper suspension point. A preferable location for an upper suspension point is Cooper's ligament on the posterior side of the pubis. Driving a needle into Cooper's ligament is difficult however. The suture needles must be adroitly manipulated while being gripped very tightly which requires both a superior needle driver and careful technique. It is not easy to get the proper angular relationships between the needle and the ligament, and the ligament is very tough.

One method to avoid these difficulties uses bone anchors in the pubic symphysis (the firm fibrocartilaginous joint between the two pubic bones) or the adjacent pubic bone. In some bone anchor techniques, the anchors are placed percutaneously, while in other techniques the anchors are placed from within the dissected retropubic space, the so-called space of Retzius. Although these techniques have been shown to work, some patients have developed undesirable complications such as pubic osteitis—a painful inflammation of the pubic bone.

In another alternative to using Cooper's ligament as a suspension point, others have chosen to suspend the suture from the rectus muscle complex superior to the pubis. This suspension point is typically used in needle suspension techniques like the Stamey procedure. However, suspension from the rectus muscle complex is typically less secure than suspension from Cooper's ligament or the pubic symphysis.

Another drawback to needle suspensions is that they are usually done blindly. The space of Retzius (retropubic space) is not dissected and, thus, there is no internal visualization of either upper or lower fixation points during the procedure. The needles are usually driven from the suprapubic area through the periurethral tissue into the vagina. Guidance of the needle is by palpation from the vagina, often with the aid of a Foley catheter. Although shown to work, these blind procedures have generally had unacceptable complication rates.

In addition, needle suspension procedures have generally required the suture to be tied from within the vagina, although some practitioners have tied subcutaneously over muscle tissue in the suprapubic region. Transvaginal lower fastenings of the suture have the advantage of utilizing the full thickness and strength of the anterior vaginal tissue layer for purposes of lifting the bladder neck. However, these transvaginal techniques require the epithelialization process to reestablish the sterility barrier between the vagina and the space of Retzius. Requiring both the knots and the tag ends of the suture to be epithelialized to assure healing might be termed optimistic. Certainly there have been instances where this has not occurred properly and further intervention was required.

Methods of lower fixation using less than full vaginal wall thickness for purposes of lower suture fastening have been used to avoid the transvaginal epithelialization controversy, but have also been reported to result in suture pullout. When less than full thickness sutures are placed in the periurethral tissue, practitioners therefore often take more than one suture pass in order to get a better bite of tissue. Needle driving in the periurethral tissue is again not easily done because of the difficult angular relationships and the extensive needle manipulation required.

Once the suture is anchored above and below, by whatever means, a suture knot must be tied and properly tensioned. This is simple if the knots are tied in the vagina, however, as noted above, this location risks uncertainty related to complete epithelialization. If tied subcutaneously in the suprapubic area, the knotting again is simple but risks the uncertainty of muscle anchoring. If Cooper's ligament is used for the upper anchor point, the ideal location for the knot is in between the upper and lower anchor points, but this is difficult by conventional laparoscopic means. Either cumbersome extracorporeal techniques are used with their tissue sawing disadvantages, or very skill intensive intracorporeal techniques are employed. With either of these, suture tensioning is difficult and the bladder neck must generally be elevated manually to the proper position through the vagina in order to achieve the proper suspension position. This requires an assistant, which undesirably results in either the knot tying or tensioning being left to hands less skilled than those of the surgeon.

Therefore, given the uneven range of surgical skills, laparoscopic experience and technique preferences among practitioners, it would be desirable to have a bladder neck suture suspension procedure and instrumentation that both minimizes specialized surgical skills and provides surgical efficacy, and includes a means of easy and proper placement of the upper and lower suspension points that are reliable from a pull-out standpoint and a means of easily tying and tensioning the sutures once they are anchored at the suspension points.

SUMMARY OF THE INVENTION

The bladder neck suture suspension procedure and instrumentation of the present invention serves to both minimize the need for specialized surgical skills and provide surgical efficacy. The surgical instrument of the present invention combines a knot tying device mounted over a suture passing device. The suture passer incorporates a grasper at its tip for purposes of passing a suture through body tissue as desired. The knot tying device is used to suture intracorporeally under tension using sliding knots such that the tension can be increased incrementally as the surgeon tests the elevation of the bladder neck by feel. The bladder neck suture suspension procedure utilizes the combined suture passer and knot tying device to provide upper and lower suspension points by anchoring a suture in Cooper's ligament and, transvaginally, in the anterior vaginal wall. The surgical instrument is then used to tie and tension a knot intracorporeally in the retropubic space between the upper and lower suspension points.

An object of this invention is to provide an improved bladder neck suture suspension procedure.

Another object of this invention is to provide an improved surgical instrument that facilitates a laparoscopic bladder neck suture suspension procedure.

Further objects and advantages of the present invention will become apparent from a consideration of the drawings and ensuing description.

DESCRIPTION OF THE PREFERRED EMBODIMENT

Referring now in detail to the drawings, FIGS. 4–10 will be utilized to describe a novel bladder neck suture suspension procedure of the present invention that suspends the bladder neck from Cooper's ligament above to the anterior vaginal wall adjacent the urethra just under the floor of the bladder in the retropubic space in a trans-vaginal fashion. However, reference will be made first to FIGS. 1–3 which illustrate a novel surgical instrument that facilitates the novel bladder suspension procedure of the present invention.

Figure 1:
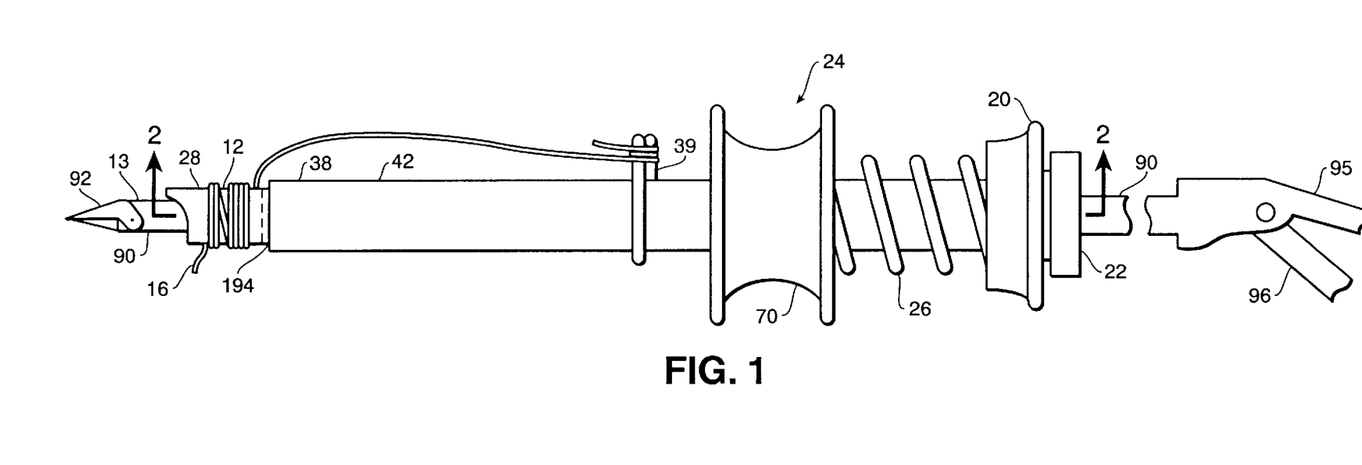
FIG. 1 is a plan view of a surgical instrument of the present invention.
Figure 2:
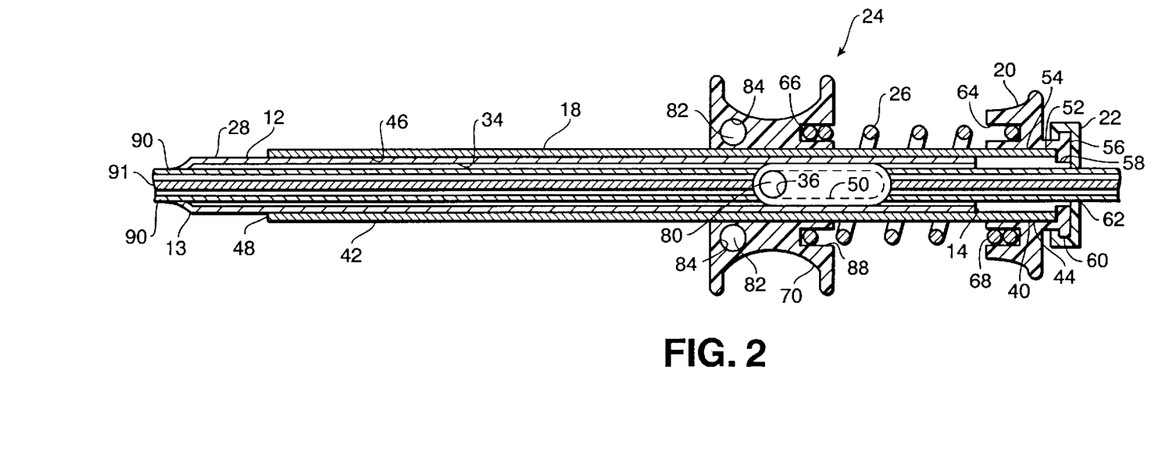
FIG. 2 is a partial cross-sectional view of the surgical instrument shown in FIG. 1 taken along line 2—2 of FIG. 1.
Figure 3:
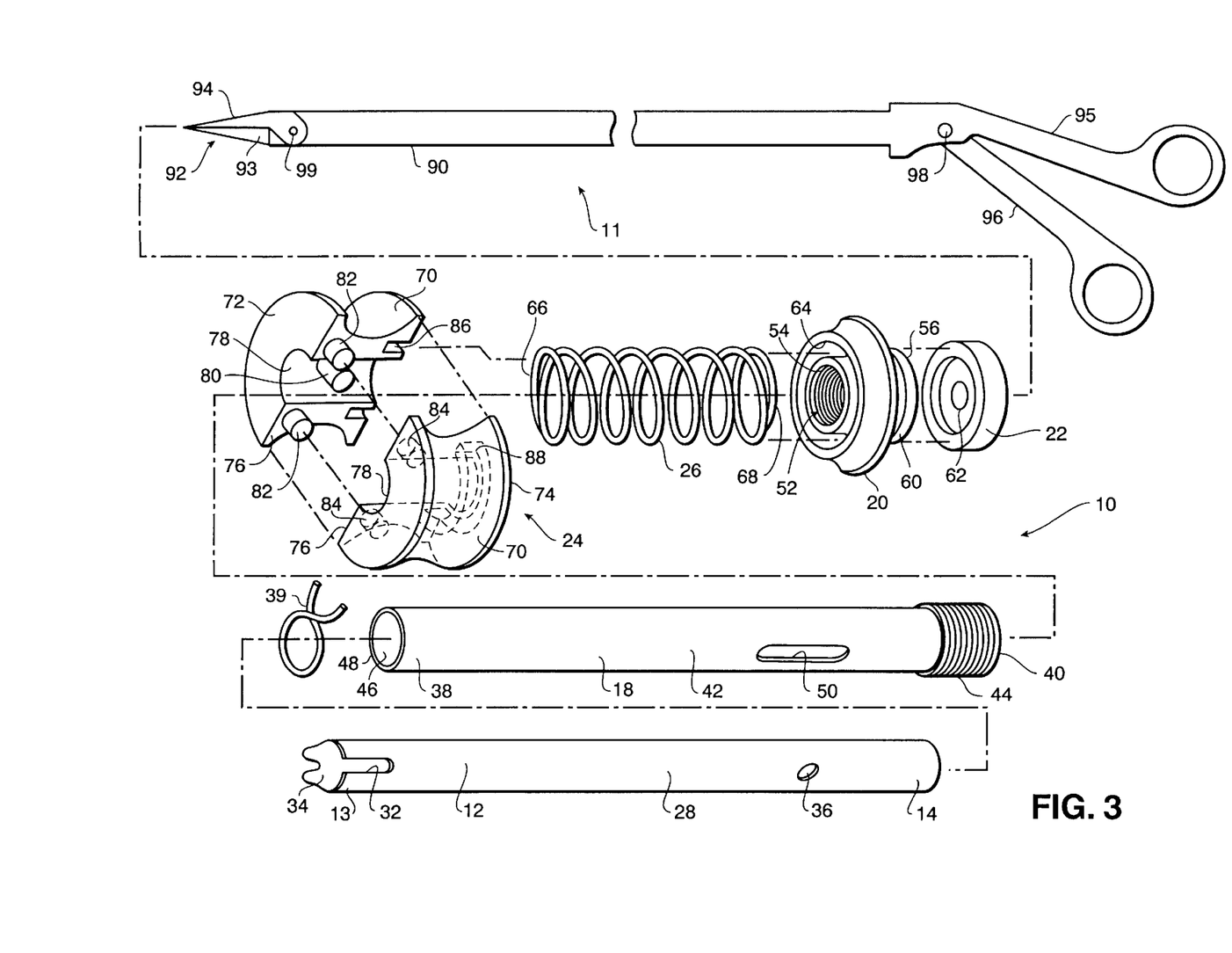
FIG. 3 is an exploded view, partially in perspective, of the surgical instrument shown in FIG. 1.

FIGS. 1–3 show a surgical instrument that combines a knot tying device 10 with a suture passing device 11. The knot tying device is comprised of a tubular rod 12 with opposite ends 13, 14 and a length of suture material 16 wrapped around one end. In addition to the inner rod 12, the knot tying device 10 also comprises an outer rod 18 concentrically sharing an axis with the inner rod 12, an annular shoulder 20 with a sealing cap 22, a manual handle 24 and a spring 26.

First referring to the inner rod 12 of the instrument, the inner rod 12 has a longitudinal length with a first, distal end 13 and a second, proximal end 14. The inner rod 12 is provided with a cylindrical exterior surface 28 that extends between the opposite distal and proximal ends 13 and 14. The rod distal end 13 is formed to serve as a knot pusher and to be used in manipulating a sliding knot, like a Roeder's knot, along a length of suture material. A longitudinal slot 32 may be provided in the rod distal end 13 to assist in visualization of the knotting process. The inner rod 12 also has a cylindrical interior bore 34 that extends completely through the rod between its distal and proximal ends 13 and 14. A circular opening 36 extends through the inner rod 12 from the exterior surface 28 to the interior bore 34.

The length of suture material 16 extends from a proximal, free end of the suture along the length of the knot tying device 10 and is wrapped in a desired pattern of loops on the distal end 13 of the inner rod 12 forming the elements of a sliding knot. From the pattern of loops wrapped on the inner rod 12, the length of suture material 16 then continues to its free, distal end. The manner in which the length of suture material 16 is wrapped on the knot tying device 10 in preparation for use of the instrument will be described later in this specification.

The outer rod 18 extends between a first, distal end 38 to a second, proximal end 40. The outer rod 18 also has a cylindrical exterior surface 42 except for external screw threading 44 formed on the exterior surface 42 adjacent the proximal end 40 of the rod 18. The outer rod 18 also has a cylindrical interior bore 46 extending completely through the rod 18 between its distal and proximal ends 38, 40. The interior diameter of the bore 46 generally matches the exterior diameter of the inner rod 12 enabling the inner rod 12 to be received in the interior bore 46 of the outer rod 18 for sliding, reciprocating movement therein. At the outer rod distal end 38, the annular end face 48 of the rod 18 surrounds the exterior surface 28 of the inner rod 12 in close conformity. This enables the annular end face 48 to slide the loops of suture material 16 wrapped over the exterior surface 28 of the inner rod 12 over the inner rod exterior surface 28 and off the distal end 13 of the inner rod 12 as the inner rod 12 is reciprocated into the interior bore 46 of the outer rod 18. An elongated opening or slot 50 extends through the outer rod 18 from the exterior surface 42 to the interior bore 46.

The annular shoulder 20 is screw threaded on the proximal end 40 of the outer rod 18. Alternatively, the shoulder 20 could be silver soldered in place on the outer rod 18. The shoulder 20 also has an interior bore 52 with internal screw threading 54 that is complementary to the external screw threading 44 of the outer rod distal end 40. An end wall 56 of the shoulder 20 has a small diameter opening 58 extending therethrough communicating with the interior bores of the concentric rods 12, 18. A circular flange 60 surrounds the periphery of the end wall. An elastic sealing cap 22 is fitted over the circular flange 60 and covers over a portion of the end wall opening 58. The sealing cap 22 has a center opening 62 that communicates with the end wall opening 58 but is smaller in diameter and area than the end wall opening 58. At the opposite end of the shoulder 20 an annular groove 64 is formed completely surrounding the exterior surface of the outer rod 18.

The coiled spring 26 is received over the exterior surface 42 of the outer rod 18. The spring 26 has opposite distal 66 and proximal 68 ends. The proximal end 68 of the spring 26 is nested in the annular groove 64 of the shoulder 20.

The handle 24 is mounted on the exterior surface 42 of the outer rod 18 for sliding, reciprocating movement thereon. The peripheral surface 70 of the handle 24 is given a general concave configuration that enables the handle 24 to be gripped easily between adjacent fingers of a surgeon's hand. To facilitate assembly of the handle 24 onto the outer rod 18, the handle 24 is formed in two halves 72, 74 best seen in FIG. 3. The two handle halves are formed with flat mating surfaces 76 with semicircular recesses 78 extending through the middle of the flat mating surfaces. The curvature of the semicircular recesses 78 conforms to the cylindrical exterior surface 42 of the outer rod 18 enabling the two handle halves 72, 74 to come together and easily slide over the exterior surface 42 of the outer rod 18. A cylindrical pin 80 extends from the semicircular recessed surface 78 of one of the handle halves. The length and diameter of the pin 80 is determined so that it will extend through the elongated slot 50 in the side of the outer rod 18 and into the circular opening 36 in the side of the inner rod 12, thereby connecting the handle half 72 or 74 to the inner rod 12. The flat surface 76 of one of the handle halves 72 has an additional pair of projecting pins 82 thereon. The flat surface of the mating handle half 74 has a pair of holes 84 recessed therein dimensioned to receive the pair of pins 82 of the other handle half 72 in assembling the two handle halves 72, 74 together over the exterior surface of the outer rod. End faces of the handle halves 72, 74 that face the annular shoulder 20 when assembled over the outer rod 18 have semicircular grooves 86, 88 formed therein that together form a circular groove in the handle end face when the two handle halves are assembled together. The circular groove formed is dimensioned to receive the distal end 66 of the coiled spring therein.

The component parts of the knot tying device 10 of the present invention are easily assembled together and disassembled after use to enable sterilization of each of the parts. In assembling the component parts together, the inner rod 12 is first inserted into the interior bore 46 of the outer rod 18 and is positioned so that the hole 36 in the side of the inner rod 12 corresponds to the elongated slot 50 in the side of the outer rod 18. Next, the two handle halves 72, 74 are assembled over the exterior surface of the outer rod 18 so that the projecting pin 80 on the semicircular recess of the one handle half extends through the elongated slot 50 of the outer rod 18 and into the opening 36 of the inner rod 12. The length of the projecting pin 80 is determined so that it is sufficiently long to extend through the elongated slot 50 of the outer rod 18 and into the opposed hole 36 of the inner rod 12 without extending into the interior bore 34 of the inner rod 12. In this manner, the pin 80 does not obstruct the interior bore 34 of the inner rod 12. In assembling the two handle halves 72, 74 together, the pair of pins 82 on the flat surface of the one handle half 72 are inserted into the pair of holes 84 in the other handle half 74. The handle halves are assembled together so that the semicircular grooves 86, 88 in their end faces face toward the proximal ends of the outer and inner rods 12, 18.

Next, the distal end 66 of the coiled spring 26 is inserted into the semicircular grooves 86, 88 formed in the handle halves 72, 74 and thereby secures the two handle halves together in their assembled condition around the exterior surface 42 of the outer rod 18. The annular shoulder 20 is then screw threaded onto the screw threading 44 of the outer rod 18. As the annular shoulder 20 is screw threaded onto the outer rod 18, the coiled spring proximal end 68 is inserted into the annular groove 64 of the shoulder 20. When the annular shoulder 20 is threaded to its furthest extent onto the distal end 40 of the outer rod 18, the coiled spring 26 will be slightly compressed.

From the above described assembly of the knot tying device 10, it should be apparent that the slightly compressed spring 26 will bias the handle 24 away from the annular shoulder 20. By the connection of the handle 24 to the inner rod 12 through the pins 80, the coiled spring 26 will also bias the inner rod 12 to its extended position relative to the outer rod 18 exposing a portion of its exterior surface 28 adjacent the distal end 13 of the inner rod 18.

One useful suture passing device 11, which is disclosed in U.S. Patent No. 5,496,335, issued on Mar. 5, 1996, is comprised of a tubular rod 90, a grasper 92 coupled to the distal end of the tubular rod 90, and scissor handles 95, 96 coupled to the proximal end of the tubular rod 90. An actuating rod 91 concentrically sharing an axis with and located internal to the tubular rod 90, is coupled to the scissor handle 96 and an upper jaw 94 of the grasper 92. As the scissor handle 96 pivots about the pivot 98 the actuating rod 91 is actuated and, thus, acts to pivot the jaw 94 about pivot 99. This movement acts to open and close the jaws 93, 94 of the grasper 92 enabling the grasper 92 to grasp and release the suture 16. The grasper 92 is shaped to be needle sharp when the jaws 93 and 94 are closed to enable the suture passing device 11 to pierce tissue and pass a suture therethrough. Other embodiments of the suture passing device would be equally suitable.

To assemble the suture passing device 11 with the knot tying device 10, the distal end of the suture passing device 11 is inserted into the interior bore 34 of the inner rod 12 through the center opening 62 of the sealing cap 22. The suture passing device 11 is extended through the internal bore 34 of the inner rod 12 positioning the grasper 92 adjacent the distal end 13 of the inner rod 12 and the scissor handles 95, 96 adjacent the proximal end 14 of the inner rod 12. The outer diameter of the tubular rod 90 is smaller, but substantially equal to the interior bore 34 of the inner rod 12 and substantially equal to the diameter of the center opening 62 in the sealing cap 22. This allows for sliding, reciprocating movement and other manipulations of the suture passing device 11 within the inner rod 12 and allows the knot tying device 10 to follow the path of the suture passing device 11 through the pierced tissue. The tubular rod 90 of the suture passing device 11 is sufficiently long so that the grasper 92 can be extended out beyond the distal end 13 of the inner rod 12. The length of the tubular rod 90 of the suture passing device 11 may vary depending of the procedure in which it is to be utilized.

The component parts of the surgical instrument may be constructed of any materials acceptable for use in surgical instruments. Additionally, the dimensions of the component parts of the instrument shown in the drawing figures are chosen to better illustrate the component parts of the invention and are not to scale and should not be interpreted as limiting. The dimensions of the component parts of the surgical instrument may be varied to best suit the embodiment of the surgical instrument of the invention shown in these drawing figures to any particular surgical operation.

In use of the combined knot tying 10 and suture passing 11 surgical instrument of the present invention, a length of suture material 16 is first wrapped in a desired pattern of loops on the inner rod exterior surface 28 projecting from the outer rod distal end 38. The free, proximal end of the length of suture 16 is held at the proximal end of the knot tying device 10, or the right hand end as viewed in drawing FIGS. 1–2, either by the surgeon's hand or by a clamp 39. The length of suture material 16 is then extended longitudinally from its proximal end toward the exterior surface 28 of the inner rod distal end 13 projecting from the distal end 38 of the outer rod 18. On this exposed portion of the inner rod exterior surface 28, the length of suture material 16 is wrapped in a desired pattern of loops. The pattern of loops can be any pattern of loops that will produce a knot in the suture material when the suture loops are displaced off the distal end 13 of the inner rod 12 and the grasper 92 of the suture passing device 11 and the distal end of the suture material 16 are withdrawn through the center of the pattern of loops and is pulled tight. For example, the pattern of suture loops wrapped on the inner rod distal end 13 can be that of a surgeon's knot, a Roeder's knot, a modified Roeder's knot, or any other pattern of suture loops that will form a knot that will slide over the portion of the length of suture grasped by the grasper 92 when the suture passing device 11 is inserted through the centers of the loops as the loops are pushed off of the inner rod distal end 13 onto the suture passing device 11 or the grasped portion of suture 16.

After forming the desired pattern of suture loops on the inner rod distal end 13 during knot staging, the length of suture material 16 then extends to its free, distal end. This excess length of suture material 16 is needed to enable manipulation of the suture 16 by the suture passing device 11 in passing the suture 16 through the desired body tissues with the suture passing device 11.

With the instrument inserted into the body so that the distal ends of the inner 12 and outer 18 rods of the knot tying device 10 are positioned proximate to the site in which a stitch is to be made, the suture passing device 11 inserted through the interiors of the inner and outer rods 12, 18 may then be used to manipulate the free, distal end of the length of suture material 16 through body tissue as desired, and used to make a stitch in the body tissue, releasing the suture material 16 and regrasping the free, distal end of the suture 16 as necessary. After the distal end of the suture 16 is passed as desired, the suture passing device 11 and grasped length of suture 16 are pulled back into the interior bore of the inner rod 12, the length of suture 16 is thus retracted through the pattern of loops formed on the exterior surface 28 of the inner rod distal end 13. With the length of suture 16 passed through the pattern of loops and being pulled taut, and with the distal end 13 of the inner rod 12 positioned proximate to the site of the stitch, the handle 24 is then manually retracted toward the annular shoulder 20 against the bias of the spring 26 causing the annular end face 48 of the outer rod 18 to push the pattern of loops formed in the length of suture 16 off of the inner rod exterior surface 28 and over the length of suture 16 forming the knot. The knot is then snugged up about the suture 16 end and slid to tighten the stitch. The distal end 13 of the inner rod 12 may be used to manipulate the knot to tighten the stitch in the body tissue. When the stitch is correctly placed, the knot may be finally tightened by pulling the two ends adjacent the knot apart with the aid of an auxiliary grasper. The suture 16 ends may then be cut free at the knot and the suture 16 residue removed from the site of the stitch formed. The instrument may then be reloaded with another length of suture wrapped in the desired pattern of loops on the inner rod distal end 13 in preparation to form the next stitch in the body tissue.

Figure 4:
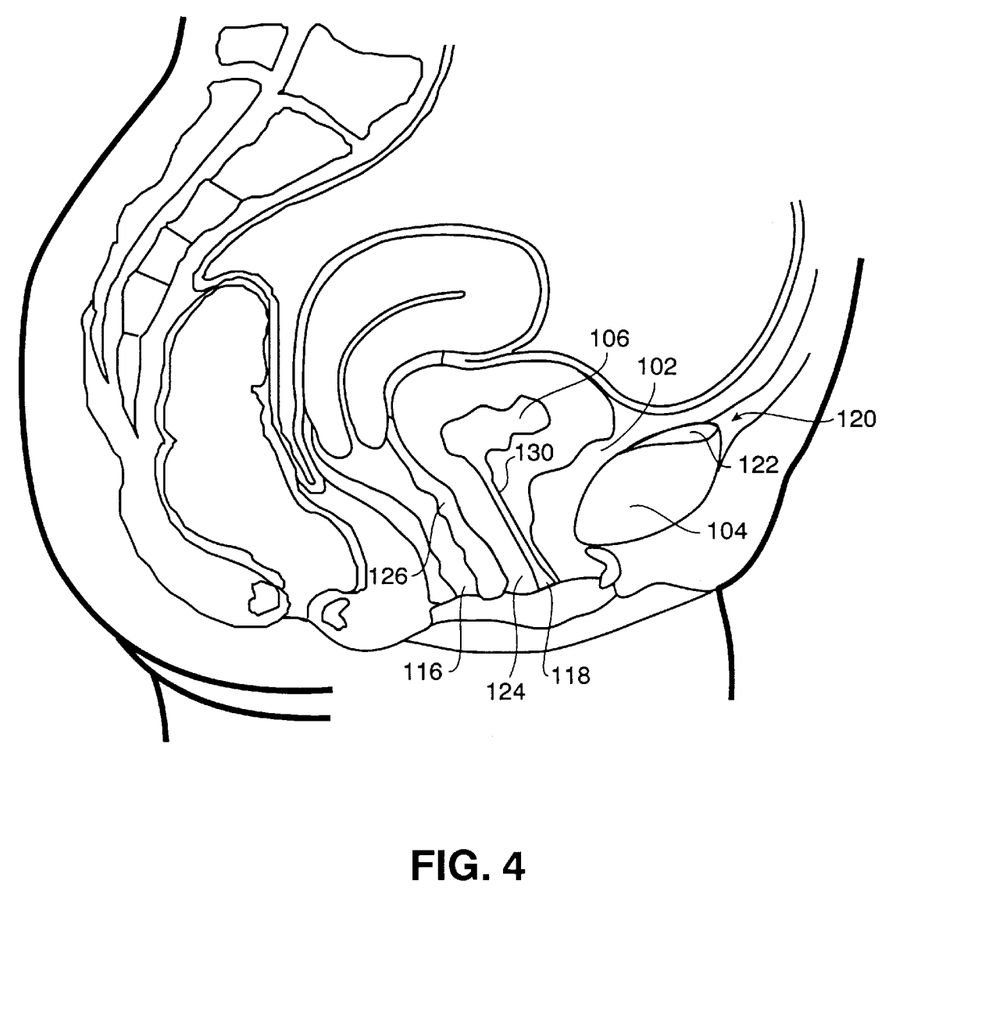
FIG. 4 is a mid-sagittal section showing the female reproductive system and surrounding structure.

Turning to FIGS. 4–10, a bladder neck suture suspension procedure is described in sequential steps using the surgical instrument described above. FIG. 4 shows a mid-sagittal section of a female patient's anatomy as presented to the surgeon. Ideally the space of Retzius 102, i.e, the space between the pubis, 104 and the bladder 106, is dissected with the help of a balloon dissector from near the umbilicus. A suitable balloon dissector is disclosed in U.S. Pat. No. 5,496,345, issued on Mar. 5, 1996, and further disclosed in U.S. patent application Ser. No. 08/570,776, filed on Dec. 12, 1995.

Figure 5:
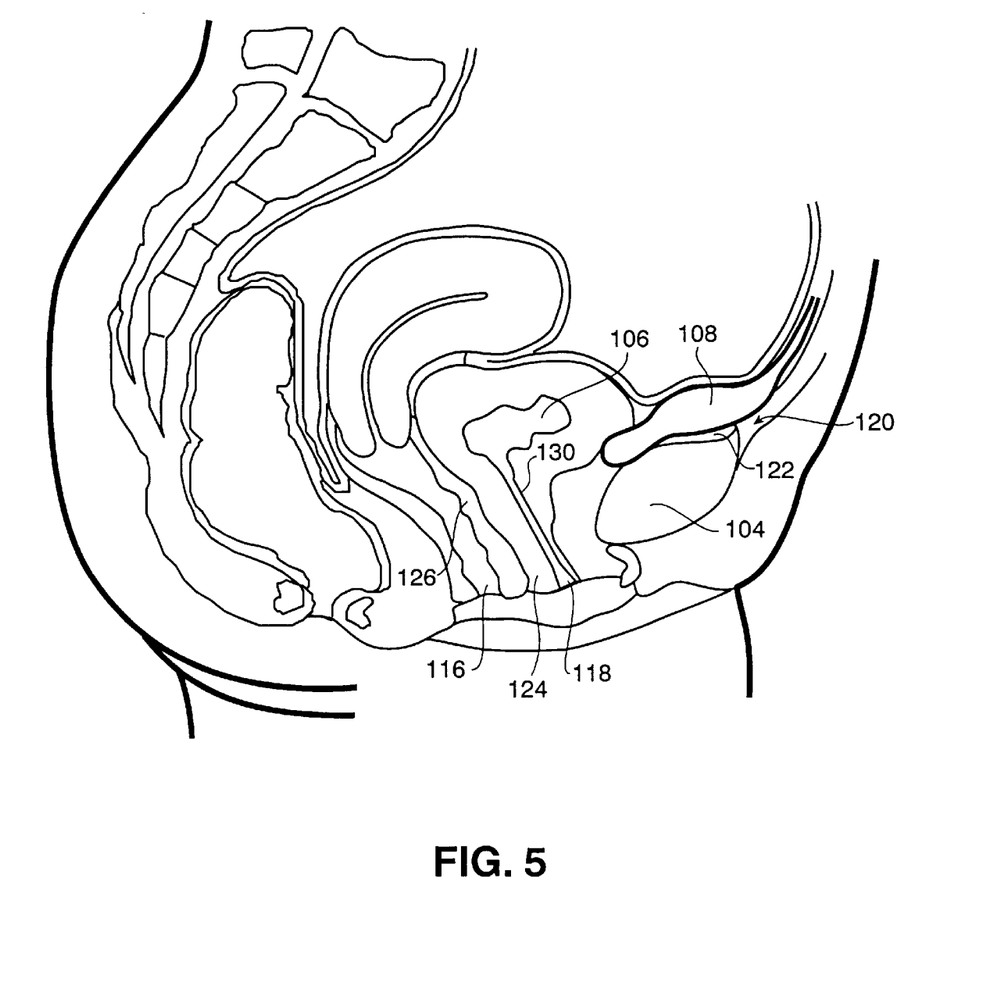
FIG. 5 shows an inflated balloon dissector in the retropubic space of the mid-sagittal section of FIG. 4.
Figure 6:
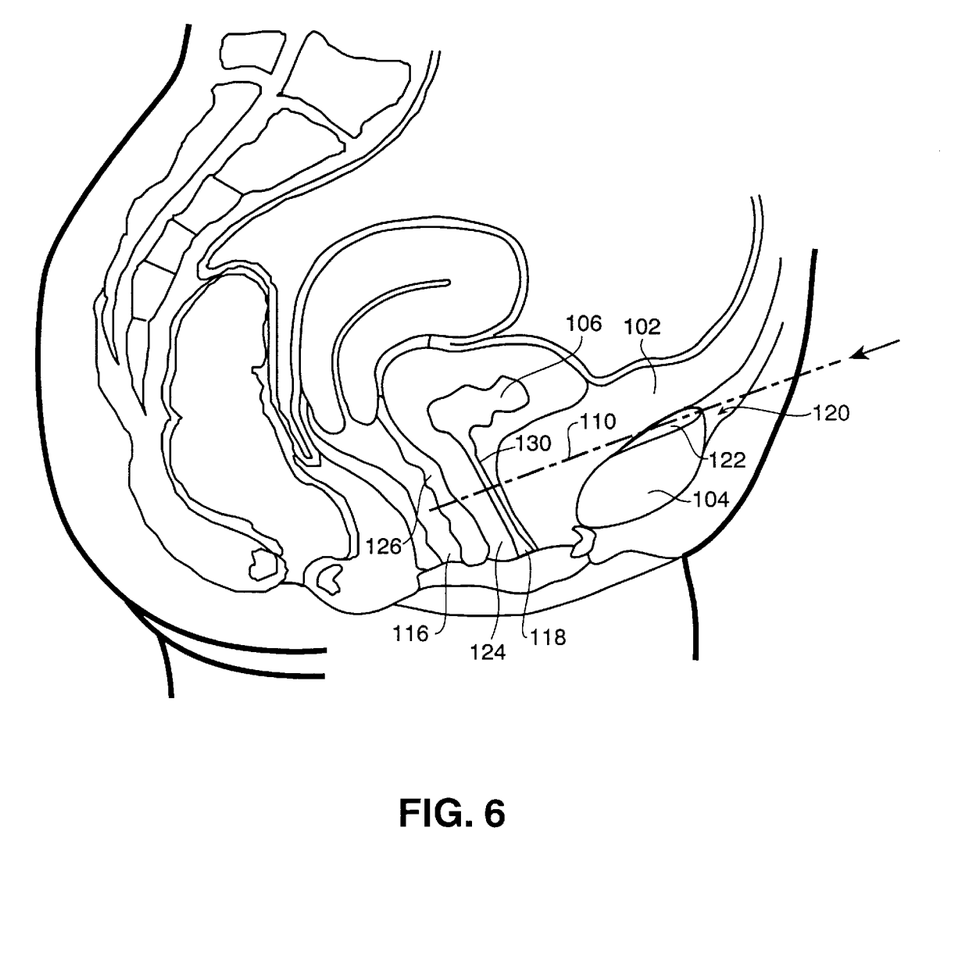
FIG. 6 shows a fully dissected retropubic space of the mid-sagittal section of FIG. 4.

FIG. 5 shows a balloon dissector 108 in place in the retropubic space 102 and partially inflated. The balloon dissector 108 may be inflated by pumping saline solution into its interior. Turning to FIG. 6, the retropubic space 102 is shown fully dissected and insufflated such that a laparoscope can be inserted from above to provide visibility for the rest of the procedure. In addition, a line 110 shows the intended path of the suture passer 11 described above through Cooper's ligament 122 posterior to the pubis 104 and on into the vagina 116, just lateral of the urethra 118.

Referring to FIGS. 7–10 for the remainder of the procedure, the knot tying device 10 with a suture 16 wound about the distal end 13 of the inner rod 12 is positioned on the suture passer 11 (shown schematically as a line) in manner described above with the distal end of the suture 16 grasped by the grasper. Under visualization in the balloon dissected retropubic space 102, the suture passer 11 is inserted through the skin in the suprapubic region 120 and makes a first pass $P_1$ passing behind the pubis 104 and through Cooper's ligament 122. After passing through Cooper's ligament 122, the suture passer 11 is passed downward through the periurethral tissue 124 and on into the vagina 116.

Figure 7:
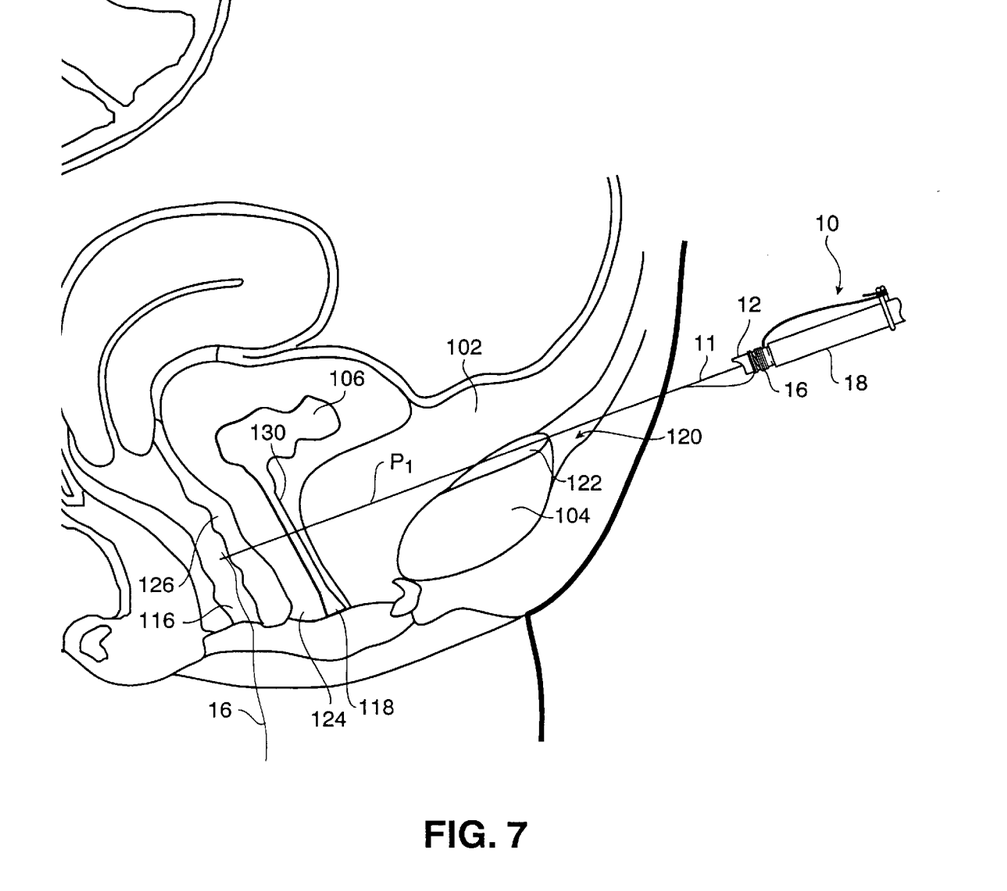
FIG. 7 shows a first pass with the surgical instrument of FIG. 1 generally through the mid-sagittal section of FIG. 6. The suture passer is shown schematically.

After the suture passer 11 has penetrated the vagina 116, the suture 16 is released from the grasper of the suture passer 11. Positioning aids may be employed as desired to maintain control of the free distal end of the suture 16. For example, a forceps can be used to grasp the suture 16 vaginally as it is released from the suture passer 11.

Figure 8:
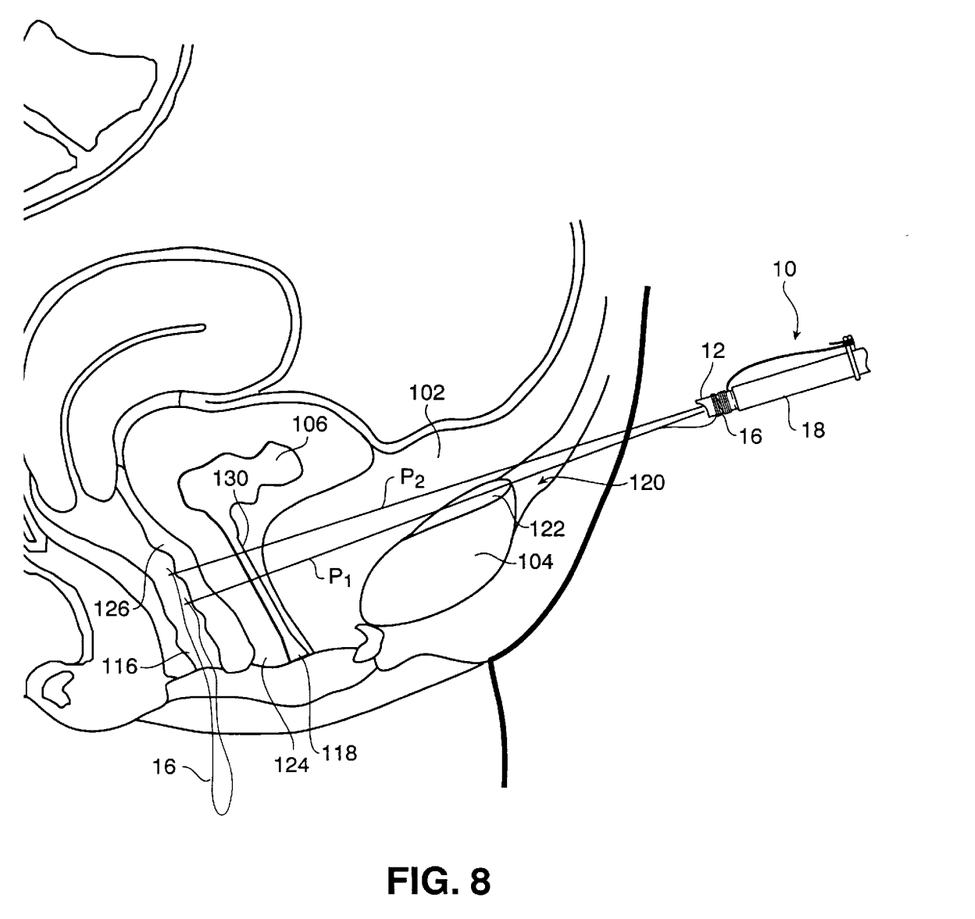
FIG. 8 shows a second pass with the surgical instrument of FIG. 1 generally through the mid-sagittal section of FIG. 6.
Figure 9:
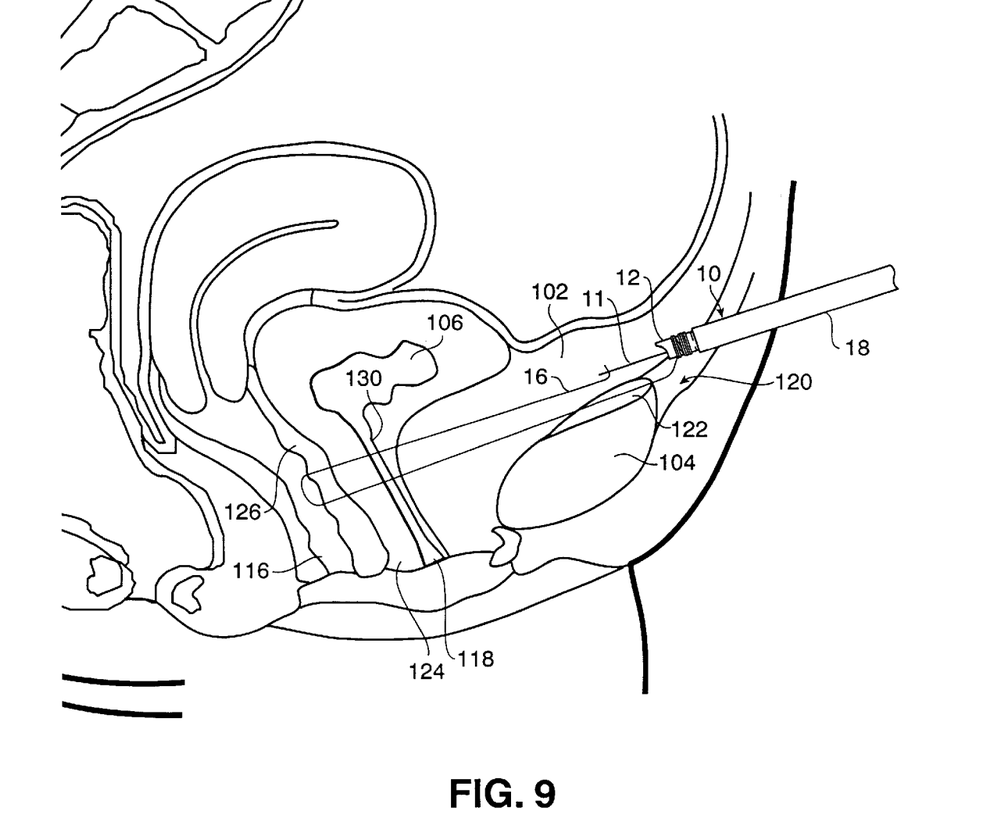
FIG. 9 shows the surgical instrument of FIG. 1 retracted into the retropubic space of the mid-sagittal section of FIG. 6 in preparation of tying a knot in a suture.
Figure 10:
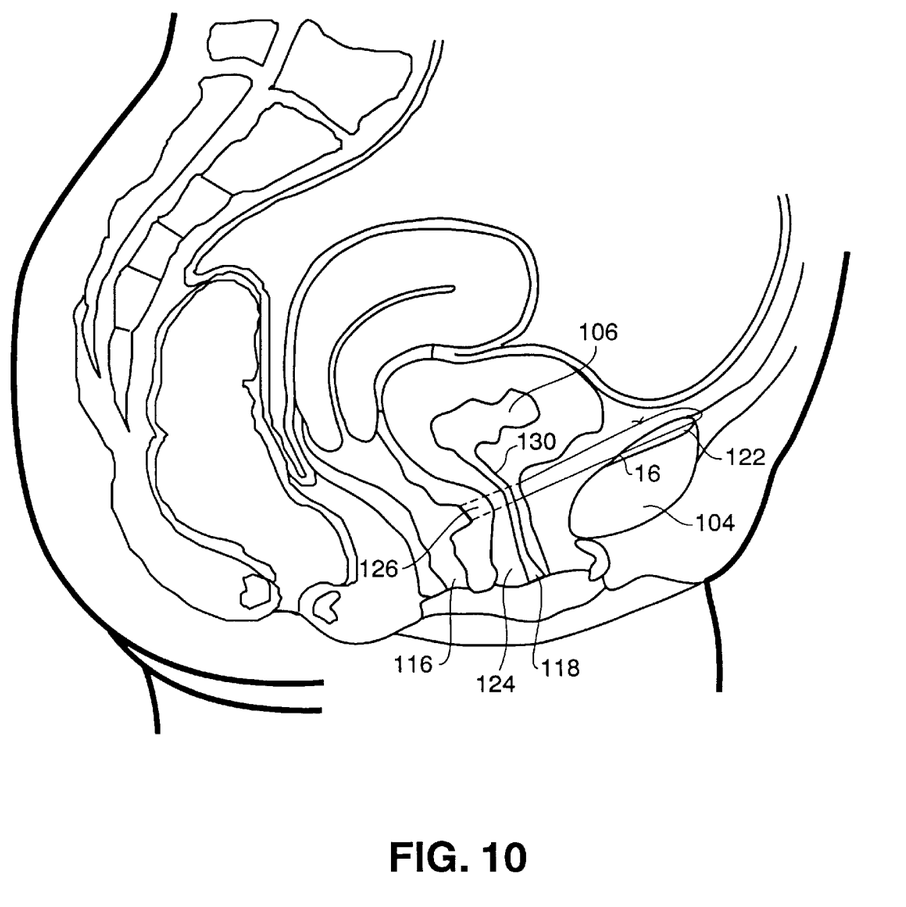
FIG. 10 shows a completed suture suspension of the bladder neck in the mid-sagittal section of FIG. 6.

With the suture 16 released from the suture passer 11, the suture passer 11 is withdrawn from the vagina 116 and out through Cooper's ligament 122. Next, the suture passer 11 makes a second pass $P_2$ and is advanced downwardly around Cooper's ligament 122 and through the periurethral tissue 124 into the vagina 116. The second pass $P_2$ passes through the anterior vaginal wall 126 at a position spaced away from the first pass $P_1$ such that an appropriate bite of the anterior vaginal wall 126 is secured. The free end of the suture 16 is regrasped and drawn back into the retropubic space 102.

With the suture 16 regrasped by the suture passer 11, the suture passer 11 is retracted back into the knot tying device 10 in the retropubic space 102. A knot is then ejected from the knot tying device 10 and the suture 16 is tensioned with the knot tying device 10 in a manner described above and, thus, positioning the knot between the upper and lower suspension points. The knot tying device 10 can be used advantageously to suture intracorporeally under tension using sliding knots such that tension can be increased incrementally as the surgeon tests the elevation of the bladder neck 130 by feel. After the suture 16 is properly tensioned, the knot is finally tightened in a manner described above. The above steps of the bladder neck suture suspension procedure of the present invention are repeated on the contralateral side of the patient to suspend the bladder neck 130 in a manner shown in FIG. 9.

In use in the bladder neck suture suspension procedure described above, the suture passer 11 should be long enough to ensure that the knot tying device 10 need not pass through Cooper's ligament 122 when the grasper of the suture passer 11 is in the vagina 116. If the suture passer 11 is not sufficiently long, an alternative to the procedure needs to be practiced to avoid passage of the knot tying device 11 through Cooper's ligament 122. Thus, once the suture passer 11 is driven through Cooper's ligament 122 on its first pass $P_1$, control of the suture 16 is given up and the suture passer 11 is withdrawn through Cooper's ligament 122. The suture 16 is then regrasped by the suture passer 11 on the other side of Cooper's ligament 122 for purposes of a periurethral stick 124. In this alternative procedure it may be desirable to introduce a second port or to use an operating laparoscope in order that another grasper may be brought to bear in order to control the free end of the suture 16. Use of this alternative procedure may be more desirable because the surgeon has greater control over a shorter suture passer 11.

The knot tying device 10 need only be long enough to reach the space adjacent to Cooper's ligament 122 for knot ejection and tensioning. If desired, or if necessary to reach the proper angles, the tubular rod 90 of the suture passer 11 can be bent and the rods 12, 18 of the knot tying device 12 can be made sufficiently flexible to follow the tubular rod 90 curve.

A further alternative to the transvaginal procedure described above may be useful in eliminating any objections to the transvaginal procedure. If the periurethral tissue 124 can be manipulated from within the vagina or by some other means, a bite may be taken without penetrating the vagina 116. Alternatively, a shallow incision may be made in the vaginal wall under the suture to aid in the epithelialization process.

The bladder neck suture suspension procedure of the present invention holds many advantages over the prior art. By making use of a suture passer 11, the use of a loose needle is eliminated. For purposes of driving the suture passer through Cooper's ligament 122, the suture passer 11 is advantageously controlled manually from outside the patient's body. The positioning of needle sticks by the suture passer 11 in Cooper's ligament 122 and the periurethral tissue 124 is done under direct visualization with the end of the suture 16 always under control. In addition, knotting is quickly accomplished using the knot tying device 10 with tension being gradually applied to a desired level, all by the surgeon, without leaving any suture knots or tag ends in the vagina. Further, the entire procedure may be reduced to a single port, two stick procedure.

Thus, the bladder neck suture suspension procedure and instrumentation of the present invention provide many benefits over the prior art. While the above description contains many specificities, these should not be construed as limitations on the scope of the invention, but rather as an exemplification of one preferred embodiment thereof. Many other variations are possible.

Accordingly, the scope of the present invention should be determined not by the embodiments illustrated above, but by the appended claims and their legal equivalents.

What is claimed:

1. A method of laparoscopically suspending a bladder neck, comprising the steps of positioning a knot tying device over a suture passer,
    grasping an end of a suture with the suture passer,
    inserting the suture passer and suture into the retropubic space,
    making a first pass with the suture passer through Cooper's ligament, the periurethral tissue and the anterior vaginal wall into the vagina,
    releasing the suture in the vagina,
    withdrawing the suture passer out of the vagina through the anterior vaginal wall and periurethral tissue, and out of Cooper's ligament into the retropubic space,
    making a second pass with the suture passer around Cooper's ligament through the periurethral tissue and the anterior vaginal wall into the vagina at a position spaced away from the first pass of the suture passer through the anterior vaginal wall into the vagina to achieve a bite with the suture of the anterior vaginal wall,
    regrasping the released suture in the vagina,
    withdrawing the suture passer and suture from the vagina into the retropubic space,
    inserting the knot tying device into the retropubic space adjacent Cooper's ligament,
    retracting the suture passer and suture into the knot tying device, and
    tying a knot in the suture.

2. The method of laparoscopically suspending the bladder neck of claim 1, further comprising the step of dissecting the retropubic space.

3. The method of laparoscopically suspending the bladder neck of claim 1, further comprising the steps of inserting a balloon dissector into the retropubic space,
    inflating the balloon dissector to dissect the retropubic space,
    withdrawing the balloon dissector from the retropubic space, and
    insufflating the retropubic space.

4. The method of laparoscopically suspending the bladder neck of claim 3, further comprising the step of inserting a laparoscope into the retropubic space to provide internal visibility.

5. The method of laparoscopically suspending the bladder neck of claim 1, further comprising the steps of inserting an auxiliary grasper into the vagina, and
    vaginally grasping the suture from the suture passer after the suture passer has penetrated the vagina on the first pass.

6. The method of laparoscopically suspending the bladder neck of claim 1, further comprising the steps of ejecting a knot from the knot tying device,
    sliding the knot with the knot tying device into position along the suture,
    tensioning the suture and the knot, and
    tightening the knot.

7. A method of laparoscopically suspending a bladder neck, comprising the steps of inserting a suture passer through a knot tying device,
    grasping an end of a suture with a suture passer,
    inserting the suture passer and suture into the retropubic space,
    making a first pass with the suture passer and suture through Cooper's ligament,
    releasing the suture from the suture passer once the suture passer and suture have passed through Cooper's ligament,
    retracting the suture passer back through Cooper's ligament,
    passing the suture passer around Cooper's ligament,
    regrasping the suture with the suture passer on the other side of Cooper's ligament,
    continuing the first pass of the suture passer and suture through the periurethral tissue and the anterior vaginal wall into the vagina, releasing the suture in the vagina, withdrawing the suture passer out of the vagina and through the anterior vaginal wall and periurethral tissue into the retropubic space, making a second pass with the suture passer around Cooper's ligament through the periurethral tissue and the anterior vaginal wall into the vagina at a position spaced away from the first pass of the suture passer through the anterior vaginal wall into the vagina to achieve a bite with the suture of the anterior vaginal wall, regrasping the released suture in the vagina, withdrawing the suture passer and suture from the vagina into the retropubic space, inserting the knot tying device into the retropubic space adjacent Cooper's ligament, retracting the suture passer suture into the knot tying device, and tying a knot in the suture.

8. The method of laparoscopically suspending the bladder neck of claim 7, further comprising the steps of inserting a balloon dissector into the retropubic space, inflating the balloon dissector to dissect the retropubic space, withdrawing the balloon dissector from the retropubic space, insufflating the retropubic space, and inserting a laparoscope into the retropubic space to provide internal visibility.

9. The method of laparoscopically suspending the bladder neck of claim 7, further comprising the steps of inserting an auxiliary grasper into the retropubic space, and grasping the suture from the suture passer after the suture passer has driven through Cooper's ligament on the first pass.

10. The method of laparoscopically suspending the bladder neck of claim 7, further comprising the steps of inserting an auxiliary grasper into the vagina, and vaginally grasping the suture from the suture passer after the suture passer has penetrated the vagina on the first pass.

11. The method of laparoscopically suspending the bladder neck of claim 7, further comprising the steps of ejecting a knot from the knot tying device, sliding the knot with the knot tying device into position along the suture, tensioning the suture and the knot, and tightening the knot.

12. A method of laparoscopically suspending a bladder neck, comprising the steps of positioning a knot tying device over a suture passer, the knot tying device including a suture mounted thereon, passing the suture passer through Cooper's ligament while the suture passer grasps the suture, passing the suture passer through the periurethral tissue and anterior vaginal wall while the suture passer grasps the suture, creating a bite of the anterior vaginal wall with the suture, and retracting the suture passer into the knot tying device while the suture passer grasps the suture.

13. The method of laparoscopically suspending a bladder neck of claim 12, further comprising the step of tying and tensioning a knot in the suture with the knot tying device.

14. A method of laparoscopically suspending a bladder neck, comprising the steps of inserting a suture passer through a knot tying device, the knot tying device including a suture mounted thereon, passing the suture passer through Cooper's ligament while grasping the suture with the suture passer, making a first pass with the suture passer through the periurethral tissue and anterior vaginal wall while grasping the suture with the suture passer, making a second pass with the suture passer through the periurethral tissue and anterior vaginal wall while grasping the suture with the suture passer, at a position spaced away from the first pass of the suture passer through the anterior vaginal wall to achieve a bite of the anterior vaginal wall with the suture, and retracting the suture passer into the knot tying device while the suture passer grasps the suture.

15. The method of laparoscopically suspending the bladder neck of claim 14, further comprising the steps of inserting an auxiliary grasper into a retropubic space, and grasping the suture from the suture passer after the suture passer has passed through Cooper's ligament.

16. The method of laparoscopically suspending the bladder neck of claim 14, further comprising the steps of inserting an auxiliary grasper into a vaginal space, and vaginal grasping the suture from the suture passer after the suture passer has penetrated the vaginal space on the first pass through the periurethral tissue and anterior vaginal wall.

17. The method of laparoscopically suspending the bladder neck of claim 14, further comprising the steps of tying and tensioning a knot in the suture with the knot tying device.

18. The method of laparoscopically suspending the bladder neck of claim 14, further comprising the steps of making an incision in the vaginal wall below the suture to aid in an epithelialization process.

19. The method of laparoscopically suspending the bladder neck of claim 14, further comprising the steps of inserting the knot holder into the retropubic space adjacent Cooper's ligament to tie a knot in the suture in the retropubic space.

* * * * *